(12) United States Patent
Swan et al.

(10) Patent No.: US 7,087,658 B2
(45) Date of Patent: *Aug. 8, 2006

(54) WATER-SOLUBLE COATING AGENTS BEARING INITIATOR GROUPS

(75) Inventors: Dale G. Swan, St. Louis Park, MN (US); Richard A. Amos, St. Anthony, MN (US); Terrence P. Everson, Eagan, MN (US); Stephen J. Chudzik, St. Paul, MN (US); Ralph A. Chappa, Prior Lake, MN (US); Sean M. Stucke, Farmington, MA (US); Peter H. Duquette, Edina, MN (US)

(73) Assignee: SurModics, Inc., Eden Prairie, MN (US)

( * ) Notice: Subject to any disclaimer, the term of this patent is extended or adjusted under 35 U.S.C. 154(b) by 34 days.

This patent is subject to a terminal disclaimer.

(21) Appl. No.: 10/745,080

(22) Filed: Dec. 23, 2003

(65) Prior Publication Data

US 2004/0137164 A1    Jul. 15, 2004

Related U.S. Application Data

(63) Continuation of application No. 09/840,406, filed on Apr. 23, 2001, now Pat. No. 6,669,994, which is a continuation of application No. PCT/US99/21247, filed on Sep. 22, 1999.

(51) Int. Cl.
*C08F 2/50* (2006.01)
*C08J 3/28* (2006.01)
*C08J 7/18* (2006.01)

(52) U.S. Cl. ............... 522/36; 522/46; 522/47; 522/48; 435/174; 435/177; 435/181

(58) Field of Classification Search ........... 522/36, 522/46, 47, 48; 427/2.1, 2.13, 2.25, 508, 427/519; 435/174, 177, 181
See application file for complete search history.

(56) References Cited

U.S. PATENT DOCUMENTS 3,927,079 A    12/1975  Houlihan et al.
4,309,453 A    1/1982   Reiner et al.
4,315,998 A    2/1982   Neckers
4,331,697 A    5/1982   Kudo et al. .............. 427/2
4,722,906 A    2/1988   Guire
4,973,493 A    11/1990  Guire
4,979,959 A    12/1990  Guire
5,002,582 A    3/1991   Guire et al.
5,290,548 A    3/1994   Goldberg et al. .......... 264/1.36
5,414,075 A    5/1995   Swan et al.
5,512,329 A    4/1996   Guire et al.
5,573,934 A    11/1996  Hubbell et al. ............ 264/4
5,612,391 A    3/1997   Chabrecek et al. ..... 351/160 R
5,714,360 A    2/1998   Swan et al.
6,358,557 B1   3/2002   Wang et al.
6,669,994 B1 * 12/2003  Swan et al. .............. 427/517

FOREIGN PATENT DOCUMENTS

WO    WO 97/16544    10/1996

OTHER PUBLICATIONS

"Radical Polymerization," C.H. Bamford, pp. 940-957 in Kroschwitz, ed., *Concise Encyclopedia of Polymer Science and Engineering*, 1990, subsection entitled "Photosensitized Initiation: Polymeric Photosensitizers and Photoinitiators,".
"A Novel Modification of Polymer Surfaces by Photografting," Tazuke et al., pp. 217-241, in *Modification of Polymers*, ACS Symposium Series 121 American Chemical Society, 1980.

* cited by examiner

*Primary Examiner*—Susan Berman
(74) *Attorney, Agent, or Firm*—Fredrikson & Byron, P.A.

(57) ABSTRACT

A method of forming a polymer layer on a support surface by the use of a coating agent and polymerizable compounds. The coating agent provides photoreactive groups adapted to attach the agent to the surface, as well as photoreactive groups adapted to remain unattached to the surface, and thus serve as photoinitiators for the activation of polymerizable compounds in order to form a polymer layer thereon. Also provided are coating agents, per se, as well as a method of using such agents and the resultant surfaces and devices fabricated therefrom.

50 Claims, 1 Drawing Sheet

WATER-SOLUBLE COATING AGENTS BEARING INITIATOR GROUPS

CROSS-REFERENCE TO RELATED APPLICATIONS

Figure 1:
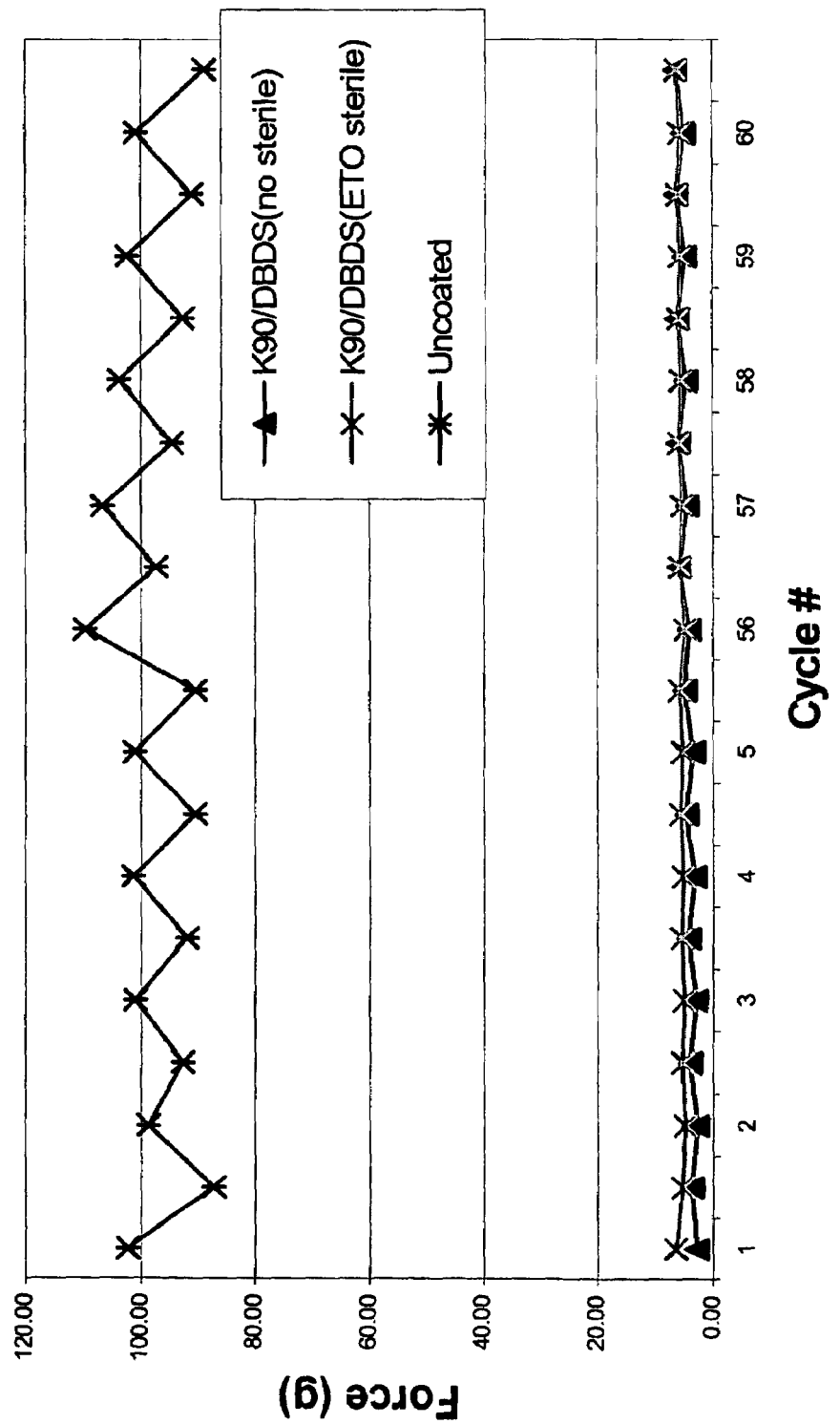

The present application is a continuation of U.S. patent application Ser. No. 09/840,406, filed Apr. 23, 2001, now U.S. Pat. No. 6,669,994, which in turn is a continuation of and claims priority to International Application No. PCT/US99/21247 (published as International Publication No. WO 01/21326), filed 22 Sep. 1999 and designating the United States, the entire disclosure of which is incorporated herein by reference.

TECHNICAL FIELD

The present invention relates to chemical and/or physical modification of the surface properties of industrially and medically important substrates. In another aspect, the present invention relates to the modification of surface properties for such purposes as providing surfaces with desired characteristics, such as hydrophilicity, lubricity, durability, and uniformity of thickness. In this aspect, the invention relates to such surface modification techniques as chemical derivatization and photoinitiated polymerization.

BACKGROUND OF THE INVENTION

The chemical modification of surfaces to achieve desired chemical and/or physical characteristics has been previously described. For example, U.S. Pat. Nos. 4,722,906; 4,973,493; 4,979,959; 5,002,582; and 5,512,329 (each of which is commonly owned by the assignee of the invention described herein, and the disclosure of each is incorporated herein by reference), relate to surface modification by the use of latent reactive groups to achieve covalent coupling of reagents such as biomolecules and synthetic polymers to various substrates. The preferred latent reactive group is typically described as a photochemically reactive functional group ("photoreactive group"). When exposed to an appropriate energy source, a photoreactive group undergoes a transformation from an inactive state (i.e., ground state) to a reactive intermediate capable of forming covalent bonds with appropriate materials.

Such latent reactive groups can be used, for instance, to first derivatize a target molecule (e.g., thermochemically), in order to then photochemically attach the derivatized target molecule to a surface. Such a sequential approach is suitable in many situations, but can lack such attributes as speed, versatility, and ease of use, particularly when used with target molecules that are inherently difficult to first derivatize or under conditions that would result in loss of biological activity.

Latent reactive groups can also be used to prepare photoactivatable heterobifunctional molecules as linking agents, e.g., having a photoreactive group at one end or portion with a thermochemical attachment group at another (see, e.g., the above-captioned '582 patent, and U.S. Pat. No. 4,309,453, Reiner et al.). Such linking agents can be used to either attach nonreactive compounds to a surface or to prime a relatively inert surface in order to render it reactive upon exposure to suitable actinic radiation.

U.S. Pat. No. 5,414,075 (commonly owned by the assignee of the present invention and incorporated by reference herein), describes the use of linking agents to prime a surface to provide the surface with photoactivatable groups. This patent describes a restrained, multifunctional reagent useful for priming a support surface, or for simultaneous application with a target molecule to a support. Reagents such as those described above, including those described in the '075 patent, are generally hydrophobic. As a result, they are of relatively low solubility in aqueous systems, thereby often limiting their usefulness in hydrophilic applications.

U.S. Pat. No. 5,714,360, also commonly owned by the assignee of the invention herein described (and incorporated herein by reference), describes a chemical linking agent comprising a di-or higher functional photoactivatable charged compound. The linking agent provides at least one group that is charged under the conditions of use, in order to provide improved water solubility, and two or more photoactivatable groups in order to allow the agent to be used as a linking agent in aqueous systems. In a preferred embodiment, the charged groups include, but are not limited to, salts of organic acids (such as sulfonate, phosphonate, and carboxylate groups), onium compounds (such as quaternary ammonium, sulfonium, and phosphonium groups), and protonated amines, as well as combinations thereof. The photoreactive groups can be provided by two or more radicals of an aryl ketone such as benzophenone.

On a separate subject, common methods of attaching a polymer to a support surface include the attachment of a preformed polymer to a surface, and grafting a polymer to a surface. For instance, Tazuke et al. discuss the modification of polymer surfaces by the use of a grafting technique that involves treating a base polymer (e.g., polypropylene) with a reacting solution that contains sensitizers (e.g., benzophenone) and a selected polymer to be grafted onto the base polymer. "A Novel Modification of Polymer Surfaces by Photografting," Tazuke et al., pp. 217–241, in *Modification of Polymers*, ACS Symposium Series 121 American Chemical Society, 1980.

On another subject, polymeric photosensitizers for initiating polymerization have been described. See, for instance, "Radical Polymerization," C. H. Bamford, pp. 940–957 in Kroschwitz, ed., *Concise Encyclopedia of Polymer Science and Engineering*, 1990. In the subsection entitled "Photosensitized Initiation: Polymeric Photosensitizers and Photoinitiators," the author states that "[p]olymeric photosensitizers and photoinitiators have been described. Many of these are polymers based on benzophenone, e.g., poly(p-divinylbenzophenone) (DVBP). Such rigid polymers are reported to be effective sensitizers since hydrogen abstraction from the backbone by excited benzophenone is less likely." Further, U.S. Pat. No. 4,315,998 (Neckers) describes polymer-bound photosensitizing catalysts for use in the heterogeneous catalysis of photosensitized chemical reactions such as photo-oxidation, photodimerization, and photocycloaddition reactions. The polymer-bound photosensitizing catalysts are insoluble in water and common organic solvents, and therefore can be readily separated from the reaction medium and reaction products by simple filtration.

To the best of Applicants' knowledge, the art does not teach, nor are there commercial products that involve, the preparation or use of nonpolymeric coating agents that are themselves attached to a surface of an article in order to initiate photopolymerizaton from the surface. Nor are there generally reagents or methods that can be used to modify such surface properties as thickness, lubricity, and stability of coating in a controlled fashion. In contrast, there remains a need for coating agents having improved water solubility, and improved versatility in use. Finally, and in spite of the developments to date, there remains a need for reagents and methods that can be used to improve the initiation of photopolymerization to grow a polymer from a support surface.

SUMMARY OF THE INVENTION

The present invention provides a method of using a coating agent to form a polymer layer on a support surface, as well as a method of priming a support surface with the coating agent itself. The invention also provides a surface coated with a polymer layer formed by such a method, as well as a primed support surface coated with the agent itself. A primed coating agent, in turn, can serve as a "linking" agent to covalently or noncovalently attach a polymer layer to the support surface. Further, the invention provides a coating system that includes a coating agent and polymerizable groups as described herein, as well as a group of novel coating agents.

In one aspect, the present invention provides a method of forming a polymer layer on a support surface, the method comprising:
  a) providing a support surface;
  b) applying to the support surface a coating agent comprising two or more photoreactive species and one or more negatively charged groups, the coating agent selected from:
    i) a conjugated cyclic diketone having attached thereto, either directly or indirectly, one or more substituents comprising negatively charged groups, and wherein each ketone group of the diketone is adapted to serve as a photoreactive moiety capable of being activated in order to provide a free radical; and
    ii) a nonpolymeric core molecule having attached thereto, either directly or indirectly, one or more substituents comprising negatively charged groups, and two or more photoreactive species, wherein the photoreactive species are provided as discrete photoreactive groups;
  wherein the photoreactive species include at least one first photoreactive species adapted, when activated in the presence of the support surface, to attach the coating agent to the surface, and at least one second photoreactive species adapted, when activated in the presence of free radical polymerizable groups, to initiate polymerization of those groups, the second photoreactive species being adapted, in the absence of such free radical polymerizable groups, to revert to a latent reactive state;
  c) illuminating the agent upon the support surface under conditions suitable to photochemically attach the coating agent to the surface by means of the first photoreactive species, and to allow the second photoreactive species to remain unbound to the support surface and to revert to their latent reactive state;
  d) providing a plurality of molecules bearing free radical polymerizable groups; and
  e) illuminating the molecules bearing polymerizable groups in the presence of the coating agent upon the support surface under conditions suitable to activate the reverted second photoreactive species of the coating agent in order to initiate polymerization of the polymerizable groups on the support surface.

The method according to the present invention provides improved control of the coating process and reduces or avoids many of the deficiencies of previous methods, e.g., low reagent solubility, and the effect on the support surface of such factors as storage history, temperature, and humidity. The present invention can also be used to reduce the occurrence of competing polymerization reactions, as between polymerizable groups on the surface and those still in solution, leading to provide increased yield upon the surface.

Various steps of the present method, including illumination to photochemically attach the coating agent to the surface, as well as providing the molecules bearing polymerizable groups, and illumination to activate photoreactive groups (e.g., reverted groups) in order to initiate polymerization, can be performed in any suitable manner, e.g., simultaneously and/or sequentially. Those skilled in the relevant art, given the present description, will also appreciate the manner in which the reaction conditions can be optimized to perform the process either simultaneously or sequentially, as desired.

The first and second photoreactive species of the present coating agent, independently, can be identical or different. Alternatively, a photoreactive species can be provided in the form of a heat activatable group (e.g., an azide group). As used herein, a photoreactive species is a group capable of being activated to form a covalent bond via hydrogen abstraction upon illumination with light of the appropriate wavelength. Such photoreactive species are preferably also capable, if unable to abstract a hydrogen, of reverting to an inactive, or "latent reactive," state. Thus, upon illumination with light of a suitable wavelength, the first photoreactive species are those that covalently bind to the support surface by abstracting a hydrogen from the surface. The second photoreactive species, on the other hand, are those that remain unreacted and thereafter revert to a latent reactive state. The second photoreactive species thereby remain available for initiating polymerization. When the first and second photoreactive species are different, they may, in a preferred embodiment, be activatable by light of different wavelengths, such that light of a particular wavelength will activate the first photoreactive species but not the second, and vice versa.

While not intending to be bound by theory, it would appear that a coating agent of the present invention tends to be of a suitable size and structure to prevent both first and second photoreactive species from attaching to a support surface. In turn, when the first photoreactive species attaches to a support surface, the second photoreactive species are prevented from also attaching to the support surface as a result of the size of the coating agent and the location of the photoreactive species on that agent.

In one embodiment, a coating agent of this invention further comprises one or more optional spacers that serve to attach a core molecule to corresponding photoreactive species, the spacer being selected from radicals with the general formula:

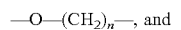, and

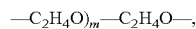, wherein n is a number greater or equal to 1 and less than about 5, and m is a number greater or equal to 1 and less than about 4.

The method of this invention can be performed using conventional compounds as coating agents, several of which are commercially available, such as anthraquinone and camphorquinone derivatives, e.g., anthraquinone sulfonic acid salt and camphorquinone sulfonic acid salt. Examples of suitable compounds of this type include conjugated cyclic diketones having attached thereto, either directly or indirectly, one or more substituents comprising negatively charged groups, and wherein each ketone group of the diketone is adapted to serve as a photoreactive moiety capable of being activated in order to provide a free radical. In a particularly preferred embodiment, however, certain coating agents of the present invention are believed to be novel in their own right. In one such embodiment, the coating agent comprises a cyclic hydrocarbon core, having attached thereto one or more substituents comprising negatively charged groups, and two or more photoreactive species, wherein the photoreactive species are provided as discrete photoreactive groups.

In any such embodiment, the photoreactive species include at least one first photoreactive species adapted, when activated in the presence of the support surface, to attach the coating agent to the surface, and at least one second photoreactive species adapted, when activated in the presence of free radical polymerizable groups, to initiate polymerization of those groups, the second photoreactive species being adapted, in the absence of such free radical polymerizable groups, to revert to a latent reactive state. The second photoreactive species, in turn, can be adapted to serve as photoinitiators, and particularly as initiators for free radical polymerization. The charged groups provide the agent with suitable water solubility to allow the agent to be used in aqueous reaction systems. Particularly preferred coating agents include negatively charged groups suitable to provide improved biocompatability and hemocompatability.

In a particularly preferred embodiment, the coating agent is selected from the compounds listed below:

| Agent | Formula |
| --- | --- |
| 4,5-bis(4-benzoyl-phenylmethyleneoxy)benzene-1,3-disulfonic acid dipotassium salt (DBDS) Compound I | |
| 2,5-bis(4-benzoyl-phenylmethyleneoxy)benzene-1,4-disulfonic acid dipotassium salt (DBHQ) Compound II | |

| Agent | Formula |
|---|---|
| Hydroquinone monosulfonic acid derivative (2,5-bis (4-benzoylphenylmethyleneoxy) benzene-1-sulfonic acid monopotassium and/or monosodium salt) Compound III | (structure shown; $K^+$ and/or $Na^+$) |

A coating agent of the invention has broad applicability, particularly since it can be used in surface modification reaction systems where previous agents have not been effective. In particular, the presence of one or more charged groups (e.g., salts of sulfonic, carboxylic and phosphoric acids) provides the agent with enhanced water solubility. This, in turn, allows the coating agent to be used in reaction systems favoring water soluble agents. A coating agent of the present invention thereby provides an improved combination of such properties as coating density and structural stability, allowing the agent to be used in a broad range of reaction systems.

Moreover, the presence of photoreactive species permits the agent to be used with a wide variety of support surfaces. The coating agent can be used alone as a coating composition for a support surface, in order to provide a surface primed with the coating agent itself. In this embodiment, the coating agent provides the surface with desirable properties of the coating agent itself, such as, for example, antithrombogenicity, lubricity, hemocomopatability, wettability/hydrophilicity, durability of attachment to the surface, biocompatability, and bacterial adhesion. Alternatively, the coating agent can be used to form a polymer layer upon the support surface. In the latter instance, the coating agent serves as a "linking" agent to covalently or noncovalently attach the polymer layer to the support surface.

In another aspect, the present invention provides a coating system comprising:

1) a coating agent as described herein, and
2) a plurality of molecules bearing polymerizable groups.

In a preferred embodiment, the molecules bearing polymerizable groups are selected from monomeric polymerizable molecules and macromeric polymerizable molecules, the monomers or macromers being either inherently hydrophilic or readily modified (e.g., by hydrolysis or solubilization) to provide hydrophilic characteristics. Such hydrophilic characteristics provide the molecules with an affinity for water, allowing the molecules to be water soluble for processing.

The present invention can be used to provide improved control over the polymerization process as compared to previous methods. This is a result of the use of photoreactive species capable of serving as a photoinitiator (e.g., photoinitiating groups) to initiate polymerization. As described herein, photoinitiating groups are provided by the coating agent itself, instead of being separately provided either in solution or by a preformed polymer to be attached to the support surface. The photoinitiating groups of the present invention are adapted to regeneratively participate in the polymerization process. In a particularly preferred embodiment, the photoreactive species are adapted to undergo reversible photolytic homolysis, thereby permitting photoreactive species that are not consumed in attachment to the support surface to revert to an inactive, or "latent" state. These photoreactive species can be subsequently activated, in order to serve as photoinitiator groups for initiating free radical polymerization. Thus, excitation of the photoinitiator is reversible and the group can return to a ground state energy level upon removal of the energy source. Particularly preferred photoinitiators are those groups that are subject to multiple activation in aqueous systems and hence provide increased coating efficiency.

In one embodiment, the coating agent can be applied to a support surface through activation of the first photoreactive species, thereby providing a primed surface comprising the support having a coating agent attached thereto. The primed surface can be illuminated to activate the second photoreactive species in the presence of molecules bearing polymerizable groups. The second photoreactive species serve as photoinitiators for free radical polymerization of the polymerizable groups of the molecules. In this embodiment, the coating agent functions to attach the resulting polymer layer to a support surface, with the polymer grown in situ upon the coating agent layer.

A coating agent of the present invention is preferably selected from the group anthraquinone sulfonic acid salt, camphorquinone sulfonic acid, hydroquinone monosulfonic acid derivatives, 2,5-bis(4-benzoylphenylmethyleneoxy) benzene-1,4-disulfonic acid dipotassium salt, and 4,5-bis(4- benzoylphenylmethyleneoxy) benzene-1,3-disulfonic acid dipotassium salt. The resulting polymer layer of the present invention provides an optimal combination of such properties as uniformity of thickness, lubricity, hemocompatability, wettability/hydrophilicity, durability of the coating agent attachment, biocompatability, and bacterial adhesion.

DETAILED DESCRIPTION

The present invention provides a method of forming a polymer layer on a support surface, the method comprising providing a support surface, applying to the support surface a coating agent comprising two or more photoreactive species and one or more negatively charged groups, illuminating the agent upon the support surface to photochemically attach the coating agent to the surface, providing a plurality of molecules bearing free radical polymerizable groups, and illuminating the molecules bearing polymerizable groups and the coating agent upon the support surface to initiate polymerization of the molecules bearing polymerizable groups on the support surface.

In one aspect, the present invention provides a coating agent comprising a nonpolymeric core molecule having attached thereto, either directly or indirectly, one or more substituents comprising negatively charged groups, and two or more photoreactive species, wherein the photoreactive species are provided as discrete photoreactive groups. In accordance with the invention, the photoreactive species comprise one or more first photoreactive species adapted to attach the coating agent to a surface, and one or more second photoreactive species adapted to initiate photopolymerization.

In one embodiment, the coating agent comprises a conjugated cyclic diketone having attached thereto, either directly or indirectly, one or more substituents comprising negatively charged groups, and wherein each ketone group of the diketone is adapted to serve as a photoreactive moiety capable of being activated in order to provide a free radical. Preferably, the conjugated cyclic diketone is a quinone selected from substituted and unsubstituted benzoquinone, camphorquinone, naphthoquinone, and anthraquinone.

In another embodiment, coating agents of this invention are believed to be novel in their own right and comprise a nonpolymeric core molecule having attached thereto, either directly or indirectly, one or more substituents comprising negatively charged groups, and two or more photoreactive species, wherein the photoreactive species are provided as discrete photoreactive groups. In a preferred embodiment, such coating agents are selected from the group 4,5-bis(4-benzoylphenylmethyleneoxy) benzene-1,3-disulfonic acid dipotassium salt (DBDS), 2,5-bis(4-benzoylphenylmethyleneoxy) benzene-1,4-disulfonic acid dipotassium salt (DBHQ), a hydroquinone derivative, an anthroquinone derivative, and a camphorquinone derivative. Optimally, the coating agent is selected from DBDS, DBHQ, and 2,5-bis(4-benzoylphenylmethyleneoxy) benzene-1-sulfonic acid mono (or di-) sodium salt.

Particularly preferred coating agents are selected from the group 4,5-bis(4-benzoylphenylmethyleneoxy) benzene-1,3-disulfonic acid dipotassium salt (DBDS), and 2,5-bis(4-benzoylphenylmethyleneoxy) benzene-1,4-disulfonic acid dipotassium salt (DBHQ).

As described herein, the coating agent generally provides a low molecular weight core molecule that provides improved coating density of the agent on a support surface of interest. Moreover, the photoreactive groups provide initiators for photopolymerization, as well as an attachment site for the agent to the surface. Finally, the charged group(s) provide improved properties such as water solubility and hemocompatability. The coating agent is thus capable of a wide variety of uses and avoids many of the limitations found in the prior art.

Suitable core molecules of the present invention include nonpolymeric radicals having a low molecular weight (e.g., 100–1000 MW). Suitable core molecules provide an improved combination of such properties as coating density, structural stability, ease of manufacture, and cost. Further, core molecules can be provided with water soluble regions, biodegradable regions, hydrophobic regions, as well as polymerizable regions. Examples of suitable core molecules include cyclic hydrocarbons, such as benzene and derivatives thereof.

Photoreactive species are defined herein, and preferred species are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being particularly preferred.

Photoreactive species respond to specific applied external stimuli to undergo active specie generation with resultant covalent bonding to an adjacent chemical structure, e.g., as provided by the same or a different molecule. Photoreactive species are those groups of atoms in a molecule that retain their covalent bonds unchanged under conditions of storage but that, upon activation by an external energy source, form covalent bonds with other molecules.

The photoreactive species generate active species such as free radicals and particularly nitrenes, carbenes, and excited states of ketones upon absorption of electromagnetic energy. Photoreactive species can be chosen to be responsive to various portions of the electromagnetic spectrum, and photoreactive species that are responsive to e.g., ultraviolet and visible portions of the spectrum, are preferred and can be referred to herein occasionally as "photochemical group" or "photogroup."

The photoreactive species in photoreactive aryl ketones are preferred, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of preferred aryl ketones include heterocyclic derivatives of anthrone, including acridone, xanthone, and thioxanthone, and their ring substituted derivatives. Particularly preferred are thioxanthone, and its derivatives, having excitation energies greater than about 360 nm.

The functional groups of such ketones are preferred since they are readily capable of undergoing the activation/inactivation/reactivation cycle described herein. Benzophenone is a particularly preferred photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source.

Photoactivatible aryl ketones such as benzophenone and acetophenone are of particular importance inasmuch as these groups are subject to multiple reactivation in water and hence provide increased coating efficiency.

The azides constitute a preferred class of photoreactive species and include derivatives based on arylazides ($C_6R_5N_3$) such as phenyl azide and particularly 4-fluoro-3-nitrophenyl azide, acyl azides (—CO—$N_3$) such as benzoyl azide and p-methylbenzoyl azide, azido formates (—O—CO—$N_3$) such as ethyl azidoformate, phenyl azidoformate, sulfonyl azides (—$SO_2$—$N_3$) such as benzenesulfonyl azide, and phosphoryl azides $(RO)_2PON_3$ such as diphenyl phosphoryl azide and diethyl phosphoryl azide. Diazo compounds constitute another class of photoreactive species and include derivatives of diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha-diazoacetates (—CO—$CN_2$—CO—O—) such as t-butyl alpha diazoacetoacetate. Other photoreactive species include the diazirines (—$CHN_2$) such as 3-trifluoromethyl-3-phenyldiazirine, and ketenes (—CH=C=O) such as ketene and diphenylketene.

Upon activation of the photoreactive species, the coating agents are covalently bound to each other and/or to the material surface by covalent bonds through residues of the photoreactive species. Exemplary photoreactive species, and their residues upon activation, are shown as follows.

| Photoreactive | Group | Residue Functionality |
|---|---|---|
| aryl azides | amine | R—NH—R' |
| acyl azides | amide | R—CO—NH—R' |
| azidoformates | carbamate | R—O—CO—NH—R' |
| sulfonyl azides | sulfonamide | R—$SO_2$—NH—R' |
| phosphoryl azides | phosphoramide | $(RO)_2PO$—NH—R' |
| diazoalkanes | new C—C bond | |
| diazoketones | new C—C bond and ketone | |
| diazoacetates | new C—C bond and ester | |
| beta-keto-alpha-diazoacetates | new C—C bond and beta-ketoester | |
| aliphatic azo | new C—C bond | |
| diazirines | new C—C bond | |
| ketenes | new C—C bond | |
| photoactivated ketones | new C—C bond and alcohol | |

The coating agents of the present invention can be applied to any surface having carbon-hydrogen bonds, with which the photoreactive species can react to immobilize the coating agents to surfaces. Examples of suitable surfaces are described in more detail below.

Photoinitiator groups useful in the present invention include those that can be used to initiate photopolymerization of polymerizable groups, by a process of free radical generation, to a desired extent and within a desired time frame. Photoinitiators are responsible for producing initiating species by the action of light energy. Free radicals can be produced by intramolecular photocleavage or hydrogen abstraction (e.g., inter- or intramolecular). Thus, according to the present invention, polymerization is generally initiated among macromers or monomers by a light-activated free-radical polymerization initiator. Preferred photoinitiators are photosensitive molecules that capture light energy and initiate polymerization of the molecules bearing polymerizable groups (e.g., macromeric polymerizable molecules or monomeric polymerizable molecules).

Examples of preferred photoinitiators include preferred photoreactive species listed above. The photoinitiator group (i.e., the second photoreactive group) can be identical to, or different from, the first photoreactive group used to attach the coating agent to a support surface. In one embodiment, the first and second photoreactive species are adapted to be independently activated by light of different wavelengths (e.g., ultraviolet light versus visible light).

Upon activation of the photoreactive species in the presence of a support surface, the second photoreactive group(s) remain unbound to the support surface and revert to their inactive state in order to serve as photoinitiator groups. While not intending to be bound by theory, it appears that the ability of a photoreactive group to remain unbound (and hence serve as a photoinitiator) is a factor, at least in part, of various reaction conditions (e.g., time and intensity of illumination wavelength, reagent concentration, etc.) and/or restrictions imposed by the size and/or structure of the coating agent itself. The photoinitiator thus remains available to be subsequently activated by a suitable energy source, and thereby initiate photopolymerization.

Photoinitiation of free radical polymerization in the present invention can take place via various mechanisms, including photochemical intramolecular photocleavage, hydrogen abstraction, and redox reactions. In a particularly preferred embodiment, photoinitiation takes place by hydrogen abstraction from the polymerizable groups.

Intramolecular photocleavage involves a homolytic alpha cleavage reaction between a carbonyl group and an adjacent carbon atom. This type of reaction is generally referred to as a Norrish type I reaction. Examples of molecules exhibiting Norrish type I reactivity and useful in a polymeric initiating system include derivatives of benzoin ether and acetophenone. For example, in a preferred embodiment wherein the coating agent of the present invention is provided in the form of a quinone having adjacent carbonyl groups (e.g., camphorquinone), photoinitiation takes place via intramolecular bond cleavage.

A second mechanism, hydrogen abstraction, can be either intra- or intermolecular in nature. A system employing this mechanism can be used without additional energy transfer acceptor molecules and by nonspecific hydrogen abstraction. However, this system is more commonly used with an energy transfer acceptor, typically a tertiary amine, which results in the formation of both aminoalkyl radicals and ketyl radicals. Examples of molecules exhibiting hydrogen abstraction reactivity and useful in a polymeric initiating system, include analogs of benzophenone and camphorquinone.

A third mechanism involves photosensitization reactions utilizing photoreducible or photo-oxidizable dyes. In most instances, photoreducible dyes are used in conjunction with a reductant, typically a tertiary amine. The reductant intercepts the induced triplet producing the radical anion of the dye and the radical cation of the reductant.

Coating agents of the present invention can be used in any suitable manner, e.g., by simultaneous or sequential attachment of the coating agent and chemical compounds (e.g., molecules bearing polymerizable groups) to a support surface. In a preferred embodiment, the method of this invention involves a two step process, involving sequential steps in which coating agent is first attached to the surface, after which compounds are polymerized thereon using the photoinitator of the attached agent. One advantage of a sequential approach is that photopolymerization of this sort allows the generation of thin polymer layers on the support surface. The resultant polymer layer is typically highly adherent, uniform in thickness, and is highly durable. Moreover, solutions used to form the polymer layer can be applied (e.g., via in solution application, dipping, spray coating, knife coating, and roller coating) to any suitable support surface of any surface morphology. The resultant polymer layer, in turn, can be adapted to cover irregular surfaces as well as smooth, relatively uniform surfaces. The polymerizable species can also be attached to the support surface simultaneously with the coating agent of the present invention, by providing suitable reaction conditions to allow such simultaneous attachment of the coating agent and polymerization of the polymerizable species.

In a particularly preferred embodiment, photoinitiation generates active species such as free radicals and particularly nitrenes, carbenes, and excited states of ketones upon absorption of electromagnetic energy. This excited photoinitiator in turn abstracts hydrogen atoms from available sources in proximity to the photoinitiator, e.g., polymerizable species, applied to the primed surface. This hydrogen abstraction thus generates a free radical site within the polymerizable species from which polymerization can proceed.

A typical free radical polymerization comprises four steps: initiation, propagation, termination, and chain transfer. In initiation, a free radical derived from an initiator adds to a monomer molecule to form an active center. Other initiating reactions include addition to the head of the molecule or hydrogen abstraction, and the reaction mechanism depends upon the structures of the radical and monomer. The propagation or growth reaction consists of the rapid addition of monomer molecules to the radical species. The most common mechanism of propagation occurs in head-to-tail fashion. However, propagation may also occur in head-to-head, tail-to-head, and tail-to-tail modes. In termination, the polymer chain stops growing by the destruction of propagating radicals. Normally, in the absence of species that destroy radicals, chain termination occurs by bimolecular interaction of radicals (e.g., radical combinations or disproportionation).

As used herein, a "charged" group generally refers to a group that is present in ionic form in solution, i.e., carries an electrical charge under the conditions (e.g., pH) of use. The charged groups are present, in part, to provide the compound with desired water solubility. Additionally, such charged groups provide a combination of such desirable characteristics as antithrombogenicity and hemocompatability.

The type and number of charged groups in a preferred coating agent are sufficient to provide the agent with a water solubility (at room temperature and optimal pH) of at least about 0.1 mg/ml, and preferably at least about 0.5 mg/ml, and more preferably at least about 1 mg/ml. Given the nature of the surface coating process, coating agent solubility levels of at least about 0.1 mg/ml are generally adequate for providing useful coatings of target molecules (e.g., polymer layers) on surfaces.

The coating agent of the present application can thus be contrasted with many coating agents in the art, which are typically considered to be insoluble in water (e.g., having a comparable water solubility in the range of about 0.1 mg/ml or less, and more often about 0.01 mg/ml or less). For this reason, conventional coating agents are typically provided and used in solvent systems in which water is either absent or is provided as a minor (e.g., less than about 50% by volume) component.

Examples of suitable charged groups include salts of organic acids (e.g., sulfonate, phosphonate, and carboxylate groups), as well as combinations thereof. A preferred charged group for use in preparing coating agents of the present invention is a sulfonic acid salt, e.g., derivatives of $SO_3^-$ in which the counterion is provided by any suitable positively charged species, e.g., as a potassium or sodium ion.

In one embodiment, the coating agent of the present invention further includes optional spacers between the nonpolymeric core molecule and one or more of the photoreactive species. A spacer is provided in situations when it is desired to provide more distance between the photoreactive species and the core molecule. For example, it can be desirable to provide a spacer to avoid steric hindrance that may result between the core molecule and the photoreactive species, thus inhibiting the photoreactive species from forming covalent bonds with a support surface (in terms of the second photoreactive species), or from serving as a photoinitiator for polymerization (in terms of the first photoreactive species).

In one embodiment, the present invention contemplates a system comprising a coating agent as described herein, and a plurality of molecules, each bearing one or more polymerizable groups. In accordance with this embodiment, the photoinitiator group serves to initiate polymerization of the polymerizable groups, thereby forming a polymer layer that is covalently bound to the support surface of a desired article via the coating agent. As used herein, "polymerizable group" shall generally refer to a group that is adapted to be polymerized by initiation via free radical generation, and more preferably by photoinitiators activated by visible or long wavelength ultraviolet radiation.

Suitable polymerizable compounds can be used to provide polymerization products (e.g., a polymer layer resulting from free radical polymerization) that are either inherently hydrophilic or are capable of being readily modified to provide hydrophilic characteristics at appropriate reaction conditions (e.g., pH). Moreover, the polymerizable groups of such compounds, can include those adapted to participate in free-radical polymerization. Preferred compounds include at least one free-radical polymerizable component (e.g., a vinyl group), and at least one functional group with a high affinity for water. As contemplated by the present invention, such functional groups with a high affinity for water can be negatively charged, positively charged, or electrically neutral.

Suitable polymerizable compounds are selected from monomeric polymerizable molecules (e.g., organic monomers), and macromeric polymerizable molecules (e.g., organic macromers). As used herein, "macromer" shall refer to a macromolecular monomer having a molecular weight of about 250 to about 25,000, and preferably from about 1,000 to about 5,000.

Suitable polymerizable compounds can contain electrically neutral hydrophilic functional units, for example, acrylamide and methacrylamide derivatives. Examples of suitable monomers containing electrically neutral hydrophilic structural units include acrylamide, methacrylamide, N-alkylacrylamides (e.g., N,N-dimethylacrylamide or methacrylamide, N-vinylpyrrolidinone, N-vinylacetamide, N-vinyl formamide, hydroxyethylacrylate, hydroxyethylmethacrylate, hydroxypropyl acrylate or methacrylate, glycerolmonomethacrylate, and glycerolmonoacrylate).

Alternatively, suitable polymerizable compounds containing electrically neutral hydrophilic functional units include molecules whose polymers, once formed, can be readily modified (e.g., hydrolyzed by the addition of ethylene oxide) to provide products with enhanced affinity for water. Examples of suitable monomers of this type include glycidyl acrylate or methacrylate, whose polymers bear epoxy groups that can be readily hydrolyzed to provide glycol structures having a high affinity for water.

Examples of suitable monomeric polymerizable molecules that are negatively charged at appropriate pH levels include acrylic acid, methacrylic acid, maleic acid, fumaric acid, itaconic acid, AMPS (acrylamidomethylpropane sulfonic acid), vinyl phosphoric acid, vinylbenzoic acid, and the like.

Alternatively, suitable monomeric polymerizable molecules that are negatively charged at appropriate pH levels include molecules whose polymers, once formed, can be readily modified (e.g., by hydrolysis via the addition of ethylene oxide) to provide products with enhanced affinity for water. Examples of suitable monomers of this type include maleic anhydride, whose polymers bear anyhdride groups that can be readily hydrolyzed to provide carboxylic acid groups, or can be readily reacted with amines to provide amide/acid structures with high affinity for water, and polymerized vinyl esters.

Examples of suitable monomeric molecules that are positively charged at appropriate pH levels include 3-aminopropylmethacrylamide (APMA), methacrylamidopropyltrimethylammonium chloride (MAPTAC), N,N-dimethylaminoethylmethacrylate, N,N-diethylaminoethylacrylate, and the like.

Alternatively, suitable positively charged monomeric polymerizable molecules include those molecules that can be readily modified (e.g., by hydrolysis via the addition of ethylene oxide) to provide products with enhanced affinity for water as well as a positive charge, e.g., glycidyl methacrylate whose polymeric products can be reacted with amines (e.g., ethylamine), to provide hydroxyamino compounds. In some cases, these materials will contain a structural unit with an inherent positive charge, as for example with fully quaternized ammonium structures. In other cases, the positively charged structural unit will exist at certain pH values, particularly at acidic pH values.

In an alternative embodiment, the polymerizable compounds of the present invention comprise macromeric polymerizable molecules. Suitable macromers can be synthesized from monomers such as those illustrated above. According to the present invention, polymerizable functional components (e.g., vinyl groups) of the macromer can be located at either terminus of the polymer chain, or at one or more points along the polymer chain, in a random or nonrandom structural manner.

The number of free-radical polymerizable groups per molecule can be varied according to the application. For example, it can be preferable to employ a macromer with just one free-radical polymerizable unit. In other instances, however, it can be preferable to employ a macromer with more than one, e.g., two or more polymerizable units per macromer. Additionally, the macromer of the present invention can contain structural features to provide improved affinity for water in a manner typically unavailable in small molecule structures (e.g., hydrophilic poly(ethylene glycol) materials).

Examples of suitable macromeric polymerizable compounds include methacrylate derivatives, monoacrylate derivatives, and acrylamide derivatives. Particularly preferred macromeric polymerizable compounds include poly (ethylene glycol)monomethyacrylate, methoxypoly(ethylene glycol)monomethacrylate, poly(ethylene glycol) monoacrylate, monomethyacrylamidopoly(acrylamide), poly(acrylamide-co-3-methacrylamidopropylacrylamide), poly(vinylalcohol)monomethacrylate, poly(vinylalcohol) monoacrylate, poly(vinylalcohol)dimethacrylate, and the like.

Such macromers can be prepared, for instance, by first synthesizing a hydrophilic polymer of the desired molecular weight, followed by a polymer modification step to introduce the desired level of polymerizable (e.g., vinyl) functional units. For example, acrylamide can be copolymerized with specific amounts of 3-aminopropylmethacrylamide comonomer, and the resulting copolymer can then be modified by reaction with methacrylic anhydride to introduce the methacrylamide functional units, thereby producing a useful macromer for purposes of this invention.

Poly(ethylene glycol) of a desired molecular weight can be synthesized or purchased from a commercial source, and modified (e.g., by reaction with methacrylyl chloride or methacrylic anhydride) to introduce the terminal methacrylate ester units to produce a macromer useful in the process of this invention. Some applications can benefit by use of macromers with the polymerizable units located at or near the terminus of the polymer chains, whereas other uses can benefit by having the polymerizable unit(s) located along the hydrophilic polymer chain backbone.

Such monomeric and macromeric polymerizable molecules can be used alone or in combination with each other, including for instance, combinations of macromers with other macromers, monomers with other monomers, or macromers combined with one or more small molecule monomers capable of providing polymeric products with the desired affinity for water. Moreover, the above polymerizable compounds can be provided in the form of amphoteric compounds (e.g., zwitterions), thereby providing both positive and negative charges.

Coating agents as described herein can be used to modify any suitable surface. Where the latent reactive group of the agent is a photoreactive group of the preferred type, the support surface to be coated preferably provides abstractable hydrogen atoms suitable for covalent bonding with the activated group. In another embodiment, the surface can be modified (e.g., by pretreatment with a suitable reagent) to provide abstractable hydrogen atoms on the surface.

The method according to the present invention is suitable for use in connection with a variety of support surfaces, including hydrogel polymers, silicone, polypropylene, polystyrene, poly(vinyl chloride), polycarbonate, poly(methyl methacrylate), parylene and any of the numerous organosilanes used to pretreat glass or other inorganic surfaces. The photoreactive coating agents can be applied to surfaces in any suitable manner (e.g., in solution or by dispersion), then photoactivated by uniform illumination to immobilize them to the surface. Examples of suitable hydrogel polymers are selected from silicone hydrogels, hydroxyethylmethacrylate polymers, and glyceryl methacrylate polymers.

Other suitable surface materials include polyolefins, polystyrenes, poly(methyl)methacrylates, polyacrylonitriles, poly(vinylacetates), poly(vinyl alcohols), chlorine-containing polymers such as poly(vinyl) chloride, polyoxymethylenes, polycarbonates, polyamides, polyimides, polyurethanes, phenolics, amino-epoxy resins, polyesters, silicones, cellulose-based plastics, and rubber-like plastics. See generally, "Plastics," pp. 462–464, in *Concise Encyclopedia of Polymer Science and Engineering*, Kroschwitz, ed., John Wiley and Sons, 1990, the disclosure of which is incorporated herein by reference. In addition, supports such as those formed of pyrolytic carbon and silylated surfaces of glass, ceramic, or metal are suitable for surface modification.

Such materials can be used to fabricate a number of devices capable of being provided, either before, during and/or after their fabrication, with a polymer layer according to the present invention. Implant devices are one general class of suitable devices, and include, but are not limited to, vascular devices such as grafts, stents, catheters, valves, artificial hearts, and heart assist devices; orthopedic devices such as joint implants, fracture repair devices, and artificial tendons; dental devices such as dental implants and fracture repair devices; ophthalmic devices such as lenses and glaucoma drain shunts; and other catheters, synthetic prostheses and artificial organs. Other suitable biomedical devices include dialysis tubing and membranes, blood oxygenator tubing and membranes, blood bags, sutures, membranes, cell culture devices, chromatographic support materials, biosensors, and the like.

According to the present invention, surface modification can be achieved using photopolymerization (e.g., by free radical polymerization). In accordance with the present method, a selected surface is contacted with a coating agent, as described above. During and/or after application of the coating agent, the surface is illuminated with UV light of the appropriate wavelength, thereby activating the photoreactive species. The coating agent is thus immobilized to the surface, by means of the first photoreactive species (with the second photoreactive species reverting to inactive form), and excess coating agent can then be optionally washed away, leaving a surface primed with a base layer of coating agent.

The coating agent can be applied to the surface of interest in any suitable manner. For example, the coating agent can be applied by dip coating or by dispersing the agent on the surface (for example, by spray coating). Suitable methods of application include application in solution, dipping, spray coating, knife coating, and roller coating. In a particularly preferred embodiment, the coating agent is applied to the surface via spray coating, as this application method provides increased density of the coating agent on the support surface, thereby improving grafting durability.

In the sequential approach described herein, a solution containing polymerizable compounds can be applied to a primed surface. The solution can be illuminated in situ to activate the second photoreactive group(s) that serve as a photoinitiator(s), thus initiating free radical polymerization via hydrogen abstraction. In a particularly preferred embodiment, photopolymerization takes place in an inert atmosphere, since oxygen interferes with free radical polymerization. Deoxygenation can take place using an inert gas such as nitrogen.

Once the system has been deoxygenated, the surface can again be illuminated with UV light of the appropriate wavelength. This second illumination thus activates the second photoreactive group(s) serving as a photoinitiator(s) of free radical polymerization. In a preferred embodiment, illumination generates the excited state of the photoreactive group, allowing the excited molecule to abstract a hydrogen from available sources, e.g., molecules bearing polymerizable groups. Such hydrogen abstraction generates a free radical site, from which polymerization can proceed.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight In one embodiment, the invention provides a coating agent and corresponding method of using to form a polymeric layer on a surface, wherein the coating agent comprises a compound of the formula:

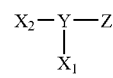

wherein $X_1$ comprises a first photoreactive species;

$X_2$ comprises a second photoreactive species;

Y comprises a nonpolymeric core molecule; and

Z comprises at least one charged group.

EXAMPLES

Example 1

Preparation of
4,5-bis(4-benzoylphenylmethyleneoxy)
benzene-1,3-disulfonic acid disodium salt (DBDS)
(Compound I)

4,5-bis(4-benzoylphenylmethyleneoxy) benzene-1,3-disulfonic acid disodium salt (DBDS) was prepared as follows. An amount (9.0 g, 0.027 moles) of 4,5-dihydroxy 1,3-benzene disulfonic acid disodium salt monohydrate was added to a 250 ml, 3 necked round bottom flask fitted with an overhead stirrer, gas inlet port, and reflux condenser. An amount (15 g, 0.054 moles) of 4-bromomethylbenzophenone (BMBP), 54 ml tetrahydrofuran (THF), and 42 ml deionized water were then added. The flask was heated with stirring under an argon atmosphere to reflux. The argon atmosphere was maintained during the entire time of refluxing.

After reflux was reached, 9.0 ml (6 N, 0.054 moles) of a sodium hydroxide solution was added through the reflux condenser. The reaction was stirred under reflux for 3 hours. After this time, a second portion of BMBP, 3.76 g (0.014 moles), and 3.6 ml (6 N, 0.022 moles) of sodium hydroxide were added. The reaction was continued under reflux for more than 12 hours, after the second BMBP addition.

The reaction mixture was evaporated at 40° C. under vacuum on a rotary evaporator to give 46 g of a yellow paste. The paste was extracted by suspending three times in 50 ml of chloroform at 40° C. for 30 minutes. A centrifuge was used to aid in the decanting of the chloroform from the solid. The solid was collected on a Buchner funnel, after the last extraction, and air dried for 30 minutes. The solid was then dried by using a rotary evaporator with a bath temperature of 50° C. at a pressure of about 1 mm for 30 minutes.

The dried solid, 26.8 g, was recrystallized from 67 ml of water and 67 ml of methanol. The dried purified product amounted to 10.4 g (the theoretical yield was 19.0 g) with absorbance of 1.62 at 265 nm for a concentration of 0.036 mg/ml.

Example 2

Preparation of
2,5-bis(4-benzoylphenylmethyleneoxy)
benzene-1,4-disulfonic acid dipotassium salt
(DBHQ) (Compound II)

2,5-bis(4-benzoylphenylmethyleneoxy) benzene-1,4-disulfonic acid disodium salt (DBHQ) was prepared as follows. An amount (15.0 g, 0.043 moles) of 2,5-dihydroxy 1,4-benzene disulfonic acid dipotassium salt was added to a 500 ml, 3 necked round bottom flask fitted with an overhead stirrer, gas inlet port, and reflux condenser. An amount (23.75 g, 0.086 moles) of BMBP, 10.0 g (0.094 moles) of sodium carbonate, 90 ml of methanol, and 90 ml deionized water were then added. The flask was heated with stirring under an argon atmosphere to reflux. The argon atmosphere was maintained during the entire time of refluxing. The reaction was stirred under reflux for 2 hours.

A second portion of BMBP, 6.25 g (0.023 moles), and 2.65 g (0.025 moles) sodium carbonate were added. The reaction was continued under reflux for 2 more hours, after the second BMBP addition.

The reaction mixture was filtered and dried to give 43.6 g of a semi-dry solid. The solid was dried to give 26.8 g of a gray powder (the theoretical yield was 31 g).

Example 3

Preparation of
2,5-bis(4-benzoylphenylmethyleneoxy)
benzenesulfonic acid sodium and/or potassium salt
(Compound E)

2,5-bis(4-benzoylphenylmethyleneoxy) benzenesulfonic acid sodium and/or potassium salt was prepared as follows. An amount (1.98 g, 0.0087 moles) of 2,5-dihydroxybenzene sulfonic acid potassium salt was added to a 100 ml, 3 necked round bottom flask fitted with an overhead stirrer, gas inlet port, and reflux condenser. An amount (4.75 g, 0.017 moles) of BMBP; 2.9 ml (0.017 moles) of 6N sodium hydroxide; 18 ml of methanol; and 14 ml of deionized water were then added. The flask was heated with stirring under an argon atmosphere to reflux. The argon atmosphere was maintained during the entire time of refluxing. The reaction was stirred under reflux for 1 hour.

A second portion of BMBP, 1.25 g (0.0045 moles), and 1.1 ml (0.0066 moles) of 6N sodium hydroxide were added. The reaction was continued under reflux for 1 more hour, after the second BMBP addition.

At the end of the reaction there were two liquid layers present. The reaction mixture had solidified 2 days later; the solid was filtered and dried to give 5.95 g of a light tan solid (the theoretical yield was 5.1 to 5.3 g).

Example 4

In-Solution Application of DBDS to Silicone Surface

An experiment was conducted to determine the feasibility of photoimmobilizing DBDS followed by grafting with methoxy PEG 1000 MMA (poly(ethylene glycol) monomethacrylate) on a silicone substrate to produce a hydrophilic coating. The resultant coating was analyzed for hydrophilicity and bacterial adherence properties.

A DBDS (Compound I) base coat was applied to a silicone substrate in the following manner. A silicone substrate was placed in approximately 2 ml of 0.5 mg/ml DBDS solution (100% water) contained in an aluminum cap. The substrate was incubated in DBDS at room temperature for approximately 5 minutes.

Following incubation, the substrate in DBDS was illuminated with a Dymax flood lamp (model no. 2000-EC, Dymax Corporation, Torrington, Conn.) which contained a doped mercury vapor lamp, to activate the photoreactive groups present in DBDS, thereby attaching DBDS to the substrate surface. The substrate was illuminated for 1 minute at an intensity of 1–1.5 mW/cm$^2$ in the wavelength range of 330–340 nm at the substrate position. Then substrate was then rinsed and placed in distilled water before grafting with poly(ethylene glycol) (PEG 1000).

Following the DBDS base coat, the substrate was placed in 8 ml of methoxy PEG 1000 MA (poly(ethylene glycol) monomethacrylate) contained in a 20 ml syringe. The PEG 1000 solution and substrate were then deoxygenated using nitrogen gas bubbling up from the bottom of the syringe for 10 minutes. After 10 minutes of sparging PEG solution with nitrogen, an EFOS UV light (Engineered Fiber Optics System, model no. 100 SS Plus, EFOS U.S.A. Inc., Williamsville, N.Y.) was placed at the top of the syringe.

The solution was illuminated with the EFOS while nitrogen gas is still bubbling up through the PEG solution. The solution was illuminated for 10 minutes at an intensity of 4–6 mW/cm$^2$, with a 320–390 nm filter at the level of the PEG solution.

Hydrophilicity

Hydrophilicity of the resulting silicone substrate was measured by determining contact angles in the following manner. Contact angles were measured using a Dynamic Contact Angle Analyzer (CAHN, model no. DCA-322). The test for wettability consists of an initialization stage followed by 3 cycles where advancing and receding angles are calculated. Each cycle contains the following program: Set speed at 100 microns/sec, Tare balance, Detect ZDOI (Zero Depth of Immersion) Advance 10 mm, Recede 10 mm, and return to zero. The sample size used for the test was a 4.1 mm (width) by 0.1 mm (thickness) by 13 mm (length). Each sample was tested in saline packing solution. Table 1 summarizes the contact angle testing completed on DBDS in-solution/PEG 1000 graft coated silicone substrates.

TABLE 1

| | Contact Angles | |
| --- | --- | --- |
| | Contact Angles (Advancing, Receding) | Angles after latex glove rubbing (Advancing, Receding) |
| Uncoated | 120, 46 | — |
| DBDS/PEG graft: | 55, 56 | 80, 51 |

These results indicate that there is a significant reduction in advancing angles, demonstrating that the samples are wettable. Although contact angles increase with latex glove rubbing on the coated substrate, there is still some hydrophilicity remaining on the silicone substrate.

Bacterial Adherence Assays

Bacterial adherence assays of the resulting silicone substrate were performed in the following manner. Two strains of *Pseudomonas aeruginosa* (American Type Culture Collection, ATCC #27853 and ATCC #15442) were examined with DBDS in-solution/PEG graft coated substrate, prepared as described above. Assays were performed of the coated substrate versus uncoated substrate. Based on the following results (Table 2 and Table 3) there is a significant bacteria reduction compared to uncoated substrate. A 98% reduction was observed with the strain ATCC #27853 when compared to uncoated substrates, and a 41% reduction was observed with the strain ATCC #15442.

TABLE 2

Bacterial Reduction - *P. aeruginosa* ATCC #27853 Adherence (n = 10)

|  | CFU/substrate ± S.D. | % Reduction compared to uncoated | P-value: one tail (comparing logs) |
|---|---|---|---|
| Uncoated | $2.25 \times 10^7 \pm 4.71 \times 10^6$ | — | — |
| DBDS with PEG graft | $3.27 \times 10^5 \pm 2.21 \times 10^5$ | 98 | 0.000232 |

TABLE 3

Bacterial Reduction - *P. aeruginosa* ATCC # 15442 Adherence (n = 5)

|  | CFU/substrate ± S.D. | % Reduction | P-value: one tail (comparing logs) |
|---|---|---|---|
| Uncoated | $6.63 \times 10^6 \pm 1.16 \times 10^6$ | — | — |
| DBDS with PEG graft | $1.08 \times 10^6 \pm 6.36 \times 10^5$ | 41% | 0.05 |

These results indicate that DBDS with PEG graft reduces bacterial adherence when the coated substrate is exposed to *Pseudomonas aeruginosa*.

Example 5

Spray Coating of DBDS on Silicone Substrate

An experiment was conducted to determine the feasibility of photoimmobilizing DBDS using a spray method to increase density of DBDS on the surface, followed by grafting with methoxy PEG 1000 MMA (poly(ethylene glycol) monomethacrylate) on a silicone substrate to produce a hydrophilic coating. The resultant coating was analyzed for hydrophilicity, durability of coating attachment, and bacterial adherence.

A silicone substrate was mounted onto a battery-operated rotator (set at 100 revolutions per minute (RPM)). The rotator was then placed under a spray and UV light source. The spray was angled at approximately 45° from horizontal and was 4.5 cm from the rounded edge of the mounting.

A DBDS solution of concentration 0.5 mg/ml in $H_2O$ was sprayed onto the substrate at a constant rate of 4–5 ml per minute. A nitrogen environment was maintained throughout the application of DBDS by introducing a nitrogen stream into the system. Simultaneously, the substrate was illuminated with an Oriel Series Q Arc Lamp (Oriel Instruments, Stratford, Conn.) which contained an Osram HBO 100 $W/cm^2$, mercury short arc doped bulb (Germany). The substrate was illuminated for 30 seconds at an intensity of 20 $mW/cm^2$ in the wavelength range of 330 nm–340 nm. The UV bulb was placed at a 45° angle from horizontal.

After DBDS was sprayed onto the substrate, three coated substrates were placed in 8 ml of a 25% methoxy PEG 1000 (v/v in water) solution contained in a 20 ml Fortuna syringe. The methoxy PEG 1000 solution and substrates were then deoxygenated using nitrogen gas bubbling up from the bottom of the syringe for 15 minutes. During the last 5 minutes, an EFOS UV light (as described above) was placed at the top of the syringe. The solution was illuminated with the EFOS while nitrogen gas was still bubbling up through the PEG solution. The solution was illuminated for 5 minutes at an intensity of 4–6 $mW/cm^2$, with a 320–500 nm filter at the level of the PEG solution.

Hydrophilicity

Hydrophilicity of the coated silicone substrates was measured by determining contact angles in the following manner. Contact angles were measured using a Contact Angle Analyzer (CAHN, model no. DCA-322). The test consists of an initialization stage followed by four cycles where advancing and receding angles are calculated. Each cycle contains the following program: Set speed at 100 microns/sec, Tare balance, Advance 2.0 mm, Tare balance, Detect ZDOI (Zero Depth of Immersion) Advance 14 mm, Recede 14 mm, and return to zero. The sample size used for the test was a 4.1 mm (width) by 0.1 mm (thickness) by 13 mm (length). Each sample was tested in saline packing solution. Table 4 summarizes the contact angle testing completed on DBDS in-solution/PEG 1000 spray graft coated silicone substrates.

Durability

The durability of the resulting coating was measured by testing contact angles after five autoclave cycles using the following conditions: Liquid Cycle, 20 minutes at 121° C. in a sealed vial filled ¾ full with 0.9% isotonic saline solution.

Another method of measuring durability is to rub the coated substrate with a latex glove and follow it up with contact angle testing, or staining in Toluidine Blue solution (Aldrich, Milwaukee, Wis.). Table 4, below, shows the data collected on substrates immediately after coating, after five autoclave cycles, and after latex glove rubbing.

TABLE 4

| | Contact Angles | | |
|---|---|---|---|
| | Initial Angles (Advancing, Receding) AVERAGE | Angles after 5 autoclave cycles (Advancing, Receding) AVERAGE | Angles after latex glove rubbing (Advancing, Receding) AVERAGE |
| Uncoated | 80, 20 | 103, 29 | 108, 40 |
| DBDS/PEG graft | 48, 23 | 37, 29 | 42, 32 |

These results indicate that a spray DBDS followed by a PEG graft improved the wettability significantly. The durability of the DBDS/PEG graft coating was also exceptional based on the contact angles after five autoclave cycles and latex glove rubbing. After five autoclave cycles and latex glove rubbing, coated samples stained in Toluidine Blue solution were much darker than uncoated control samples, indicating coating was present.

Bacterial Adherence Assays

Bacterial adherence assays of the resulting silicone substrate were performed in the following manner. Two strains of *P. aeruginosa* bacteria (ATCC #27853 and ATCC #15442), and *Staphylococcus epidermidis* (ATCC #35984) were examined with DBDS spray/PEG graft coated substrate. Both coated and uncoated substrates were tested, and the results for each were compared. Tables 5–7 below summarize the results.

TABLE 5

Bacterial Reduction - *P. aeruginosa* ATCC #27853 Adherence (n = 5)

|  | CFU/substrate ± S.D. | % Reduction | P-value (comparing logs) |
|---|---|---|---|
| Uncoated | $2.59 \times 10^6 \pm 8.53 \times 10^5$ | — | — |
| DBDS with PEG graft | $7.52 \times 10^4 \pm 5.39 \times 10^4$ | 98 | 0.00006 |

TABLE 6

Bacterial Reduction - *P. aeruginosa* ATCC # 15442 Adherence (n = 5)

|  | CFU/substrate ± S.D. | % Reduction | P-value (comparing logs) |
|---|---|---|---|
| Uncoated | $2.03 \times 10^6 \pm 8.97 \times 10^5$ | — | — |
| DBDS with PEG graft | $6.66 \times 10^4 \pm 3.76 \times 10^4$ | 96 | 0.00005 |

TABLE 7

Bacterial Reduction - *S. epidermidis* ATCC #35984 Adherence (n = 5)

|  | CFU/substrate ± S.D. | % Reduction | P-value (one tail) |
|---|---|---|---|
| Uncoated | $4.4 \times 10^6$ | — | — |
| DBDS with PEG graft | $1.87 \times 10^5$ | 96 | 0.0575 |

As shown in the above tables, the results indicate that, in each test, there was at least a 96% reduction of bacterial adherence compared to uncoated silicone substrate.

Example 6

DBDS Coating on Hydrogel Matrix

An experiment was performed to demonstrate the effectiveness of using DBDS as a coating agent on a polyvinylpyrrolidone (PVP) based, lubricious, hydrogel matrix.

The concentrations for the formulations came out of Design of Experiments (DOEs) performed with DBDS/PVP$_{k90}$ combinations. Three factors were varied for each experiment, PVP$_{k90}$ concentration (20–40 mg/ml), DBDS concentration (0.3–0.7 mg/ml), and % isopropyl alcohol (10–40% by volume IPA). From the experiments it was determined that high PVP$_{k90}$ level (40 mg/ml), high DBDS (0.7 mg/ml), and low % IPA level (10%) was the most favorable formulation for the DBDS/PVP$_{k90}$ combinations.

A solution of DBDS and PVP was prepared and applied to the surface of a polyvinylchloride (PVC) intermittent urinary catheter. This solution contained 0.7 mg/ml of DBDS and 40 mg/ml of PVP$_{k90}$ in a solvent system of 10% (by volume) isopropyl alcohol and 90% (by volume) water.

The surface of the PVC catheter was cleaned by wiping with an alcohol soaked cloth. The coating was applied to the catheter by a dip method at a speed of 1 cm/s. The coating was illuminated wet to dry with a Dymax lamp (as previously described) for 4 minutes, while the catheter was rotated.

Durability and Lubricity

To assess lubricity and tenacity of coated parts, frictional force over both the first and last 5 cycles of a 60 cycle test was evaluated. The coated catheters were evaluated by a horizontal sled style friction test method (modified ASTM D-1894, as described below).

Regenerated cellulose (Spectra/Por molecular porous membrane, MWCO: 6-8,000, flat width 50 mm, part #132665, available from Spectrum Medical Industries, Inc., Los Angeles, Calif.) was hydrated and then wrapped around a 200 gram stainless steel sled. The sheet of cellulose was clipped together tightly on the opposite side of the sled. The sled with rotatable arm was then attached to a 250 gram Chatillon Digital Force Gauge (DGGHS, 250×0.1) with computer interface. The testing surface was mounted on a 22.5 inch positioning rail table with micro-stepper motor control (Compumotor SX6 Indexer/Drive).

The parts to be tested were hydrated in deionized water and clamped onto the test surface 1 inch (or approximately 2.5 cm) apart. The hydrated cellulose covered sled was placed on top of the parts. Initial force measurements were taken while the sled moved at 0.5 cm/sec over a 5 cm section for five push/pull cycles. The sled then continued cycling over the coated samples 50 push/pull cycles at 5 cm/sec to simulate abrasion. The velocity was then decreased back to 0.5 cm/sec and the final force measurements were taken over another five push/pull cycles.

As shown in FIG. 1 below, the results show that the DBDS/PVP$_{k90}$ combination provided a superior lubricious hydrogel matrix in terms of durability. For the DBDS formulation, the grams of force remained relatively constant for all 60 cycles, indicating a durable coating.

Example 7

Partial Thromboplastin Time of Coating Agents

An experiment was conducted to determine the hemocompatability of the coating agent when attached to a support surface.

A useful test in determining the hemocompatibility of a reagent is the partial thromboplastin time (PTT) test. The PTT is a test of the intrinsic (factors VIII, IX, XI, and XII) and common (fibrinogen, prothrombin, factors V and X) pathways of coagulation. A mixture of plasma and phospholipid platelet substitute (rabbit brain cephalin) is recalcified and the time required for the appearance of fibrin strands measured.

The PTT was tested to determine whether Compound I or Compound II have the ability to extend the control PTT. A test tube of rabbit brain cephalin (Sigma #RBC) in 0.85% NaCl and a test tube of 0.02 M CaCl$_2$ was brought to 37° C. in a water bath. Dade Ci-trol coagulation control lyophilized plasma (Dade International, Inc., product no. 34224-10) was reconstituted in sterile deionized water. In 10×75 mm glass test tubes, 100 µl reconstituted plasma and 100 µl RBC were mixed and incubated at 37° C. in a water bath for 5 minutes. Next, 50 µl of sample (deionized water, a photocrosslinkable polyvinylpyrrolidone (available from SurModics, Inc., product no. PVO5), or Compound I or II) was added and mixed. While simultaneously starting a stop watch, 100 μl of 0.02 M CaCl$_2$ was added to initiate the clotting cascade. After 40 seconds had passed, the test tubes were shaken lightly, observed for fibrin formation, and the number of seconds was recorded.

All samples were tested in duplicate. The appropriate control PTT, depending upon what solvent in which the reagent was dissolved, was subtracted from the average PTT for the reagent to give the time the control PTT was extended.

The results of a PTT experiment with two different concentrations of each reagent are shown in Table 8. The polymer PVO5, which does not have any sulfonate groups, did not extend the deionized water control PTT. Compounds I and II, which contain sulfonate groups, were able to considerably extend their control PTTs at both concentrations tested. At the higher of the two final concentrations tested, Compound II is able to extend the PTT from its water control by 1 hour or more, and Compound II is able to extend the 50% IPA control PTT by 1 hour. These results show that the reagents were able to inhibit the coagulation cascade, and therefore could be beneficial for hemocompatible applications.

TABLE 8

PTT of sulfonate reagents.

| Sample | Final Concentration (mg/ml) | Solvent | Formed Clot | Average PTT (seconds) | Time Extended Beyond Control PTT (seconds) |
|---|---|---|---|---|---|
| DI H$_2$O control | — | — | yes | 53 | — |
| 50% IPA control | — | — | yes | 78 | — |
| PVO5 | 0.7 | H$_2$O | yes | 53 | 0 |
| Compound I | 0.7 | H$_2$O | yes | 117 | 64 |
| Compound II | 0.7 | 50% IPA | yes | 134 | 56 |
| Compound I | 1.43 | H$_2$O | no | >3600 | >3600 |
| Compound II | 1.29 | 50% IPA | yes | 3600 | 3522 |

Example 8

Surface Modification and Analysis of Low Density Polyethylene (PE) with Modified Sulfonate Reagents (Compounds I and II)

The polymer polyethylene was surface-modified with both DBDS (Compound I) and DBHQ (Compound II). The polyethylene substrate was obtained as flat sheets and used as ½ inch diameter discs. The coating solutions were prepared as follows: DBDS (Compound I) was dissolved at 10 mg/ml in neat water, and DBHQ (Compound II) was dissolved at 9 mg/ml in 50% (v/v) isopropanol (IPA) and 50% (v/v) water. The reagents were applied to polyethylene substrates using hand-dipping coating methods.

Before coating with the sulfonate reagents, polyethylene sheets were precoated with 1 coat of PVO5 (SurModics, Inc., as described above) 5 mg/ml in neat IPA, in order to make the hydrophobic nature of the polyethylene surface wettable so the sulfonate-containing compounds could easily be applied. The sheets were suspended vertically, immersed into PVO5 solution and withdrawn at a steady rate. Next, the sheets were air dried until the solvent was no longer visible, often within 1 minute.

The substrate with the PVO5 coat was then suspended midway between two staggered Dymax UV curing lamps, each outfitted with a Heraeus Q402Z4 bulb. At the distance of placement of the lamps, the parts received approximately 1.5 mW/cm$^2$ in the wavelength range 330–340 nm. The substrate was rotated at 3 rpm during the two minutes of illumination to ensure that the surface was evenly bathed in light.

After applying the PVO5 precoat to the substrate, 3 coats of sulfonate reagent were applied in the same manner. The coated sheets were then stored at ambient temperature until used for platelet attachment and activation assay, and surface analysis.

Two different techniques, staining and ESCA (Electron Spectroscopy for Chemical Analysis), were used to evaluate the surfaces of sulfonate-modified polyethylene to confirm the presence and uniformity of the coatings. The coated materials were stained with Toluidine Blue O, a positively charged, visible-wavelength dye. Samples were immersed in a solution of the dye (0.02% w/v in water) for 30 seconds, removed from solution, and rinsed with deionized water. The stained pieces were assessed by visual inspection for uniformity and intensity of staining.

ESCA was used to examine quantitatively the surface chemical composition of the modified substrates. Samples were analyzed with a Quantum 2000 ESCA system (Physical Electronics) using monochromatic Al X-rays. Survey spectra were collected to calculate the atomic concentrations in the surface.

Platelet Attachment and Activation from Platelet Rich Plasma

The surface-modified materials were incubated with platelet rich plasma (PRP), observed with a scanning electron microscope and photographed to determine the influence of surface chemistry on platelet attachment and activation.

Blood was collected fresh from human volunteers into 3.8% (v/v) sodium citrate solution using 9:1 ratio of blood to anticoagulant. The blood was centrifuged at 1200 rpm for 15 minutes to separate PRP from blood. The PRP was collected and kept at room temperature until used (less than 1 hour).

The test samples (½-inch circles) were placed in a 6-well plate, 1 sample per well. The PRP solution was added onto the top of the samples until the entire surface of the sample was covered, and the samples were incubated one hour at room temperature with no agitation. To quantify the platelet solution, a sample of the PRP was taken and diluted 1:100 with 1% (v/v) Oxalate Ammonium. A capillary tube was used to transfer a small amount of solution to a hemacytometer, and the sample was incubated in a covered petri dish for 30 minutes at room temperature for the platelets to settle.

The platelets were counted under a phase contrast microscope and determined to be approximately 50–100×10$^9$ platelets/L. After incubation, the PRP was removed carefully by aspiration and 3 mls of Tyrode's buffer (138-mM NaCl, 2.9-mM KCl, 12-mM sodium bicarbonate, pH 7.4) gently added to each well. The plates were agitated slightly on an orbital shaker for 15 minutes; the solution was changed and the wash repeated. The wash solution was aspirated and 2.0 ml of Karnovsky's fixative (25-mls formaldehyde, 5-mls 25% glutaraldehyde, 20-mls of a solution of 23% $NaH_2PO_4$—$H_2O$, 77% $NaHPO_4$ anhydrous) were added to each well. The plate was wrapped with parafilm and incubated overnight at room temperature with slight agitation.

The fixative was aspirated off and the samples were washed 3 times each with pure water, 15 minutes each. The samples were then dehydrated with an ethanol series of 25, 50, 75 & 100%, for 15 minutes each. The samples were kept at 4° C. in 100% ethanol until mounted (up to 4 days). Samples were mounted and coated with a 100 Angstrom sputter coating of Pd/Au and observed using a JEOL 840 scanning electron microscope. Photos were taken of different areas along the sample at several magnifications to give a representative view of each sample. The platelets were counted and judged by degree of activation and morphology.

The results of the dye binding suggested that the surface modification procedures were successful in immobilizing the sulfonate reagents on the substrate surface. Compound II and Compound I coated surfaces stained dark blue and the color was uniform. Uncoated polyethylene did not stain.

Table 9 shows results of the ESCA (Electron Spectroscopy for Chemical Analysis) measurements on the surface of uncoated and sulfonate-modified polyethylene. Polyethylene in the uncoated state should have an atomic concentration of 100% carbon (as ESCA cannot detect hydrogen atoms). The modified and unmodified samples could simply be compared by detecting sulfur on the surface of modified polyethylene due to the sulfonate groups contained in Compounds I and II.

TABLE 9

Atomic Concentration summary of PE samples (atomic %).

| Sample | [C] | [N] | [O] | [Na] | [K] | [S] |
|---|---|---|---|---|---|---|
| Uncoated control | 99.75 | 0.00 | 0.24 | 0.00 | 0.00 | 0.00 |
| Compound I | 67.39 | 1.64 | 21.54 | 0.14 | 5.74 | 3.41 |
| Compound II | 71.37 | 0.55 | 19.16 | 4.05 | 1.33 | 3.49 |

There was no presence of sulfur on uncoated polyethylene whereas on both Compound I and Compound II there was 3.41 and 3.49, respectively. Another indication that coating was successful is the presence of the appropriate counterions (e.g., sodium or potassium). ESCA results show that Compound I has potassium predominantly as a counterion, and Compound II has sodium predominantly as a counterion. This is in agreement with what counter-ion should be present for each reagent.

The SEM (scanning electron microscope) results for the platelet attachment experiments are shown in Tables 10 and 11. From the SEM photographs, surface densities of bound platelets were estimated.

The predominant platelet morphologies were observed from the SEM photographs and are summarized in Table 11.

The lowest platelet densities, other then the PVO5 coated control, were found on the Compound II modified PE. Compound II showed few numbers of platelets, which all had some spreading pseudopodia, but little or no aggregating. Compound I had similar platelet densities to those found on the uncoated control; but showed less activation and spreading. Platelets that are rounded and had less spreading were interpreted to be less activated, whereas the platelets that showed substantial aggregates and spreading were interpreted to be more activated.

TABLE 10

Average Platelet Densities on modified surfaces (platelets/cm$^2$).

| Reagent | PE |
|---|---|
| Compound I | 2000–3000 |
| Compound II | 100–200 |
| PV05 | 0–10 |
| Uncoated | 2000–2500 |

TABLE 11

Morphology of platelets attached to modified surfaces.

| Surface | PE |
|---|---|
| Compound I | Full coverage, many aggregates, little spreading |
| Compound II | Light coverage, no aggregates, most are spread |
| PV05 | Sparse coverage/none, no aggregates, no spreading |
| Uncoated | Full coverage, many aggregates, heavy spreading |

Sparse = 0–10 platelets/cm$^2$
Light = 10–100 platelets/cm$^2$
Medium = 100–1000 platelets per cm$^2$
Full = >1000 platelets per cm$^2$ Beta-Thromboglobulin Assay The surface-modified materials were incubated with PRP and the plasma was assayed for the Beta-Thromboglobulin (β-TG) released from the α-granules due to activation of the platelets. Blood was collected fresh from human volunteers into 3.8% (v/v) sodium citrate using 9:1 ratio of blood to anticoagulant. The blood was centrifuged at 1200 rpm for 15 minutes to separate PRP from blood. The PRP was collected and kept at room temperature until used (less than 1 h). The test samples (½-inch circles) were placed in a 6-well plate, 1 sample per well. The PRP solution was added onto the top of the samples until the entire surface of the sample was covered, and the samples incubated one hour at room temperature with no agitation. Control samples of plasma, for initial β-TG levels, were taken prior to incubation.

After incubation with the samples, prostaglandin E[1] (Sigma, product no. P5515) was added to each sample and the plasma was assayed with an enzyme immunoassay kit (Asserachrom American Bioproduct, product no. 0250) for the amount of β-TG released.

The surface modified with Compound I consistently showed lower levels of β-TG release than the uncoated and PVO5 controls. The β-TG release from the alpha granules is representative of platelet activation. Therefore, along with the platelet adhesion and activation experiments above, this indicates that the Compound I coating reduced the activation of platelets in contact with a polyethylene surface in vitro.

Although the present invention has been described in detail, the foregoing description is illustrative of the present invention but not considered to be limiting. Numerous variations and modifications may be effected without departing from the true scope and spirit of the invention, all of which are contemplated as falling within the scope of the appended claims.

The invention claimed is:

1. A coating system comprising:
   a) a coating agent comprising two or more photoreactive species and one or more negatively charged groups, the coating agent selected from:
      i) a conjugated cyclic diketone having attached thereto, either directly or indirectly, one or more substituents comprising negatively charged groups, and wherein each ketone group of the diketone is able to serve as a photoreactive moiety capable of being activated in order to provide a free radical; and
      ii) a nonpolymeric core molecule having attached thereto, either directly or indirectly, one or more substituents comprising negatively charged groups, and two or more photoreactive species, wherein the photoreactive species are provided as discrete photoreactive groups;
   wherein the photoreactive species include at least one first photoreactive species able, when activated in the presence of the support surface, to attach the coating agent to the surface, and at least one second photoreactive species able, when activated in the presence of free radical polymerizable groups, to initiate polymerization of those groups, the second photoreactive species being able, in the absence of such free radical polymerizable groups, to revert to a latent reactive state, and wherein the photoreactive species are independently aryl ketones; and
   b) a plurality of molecules bearing free radical polymerizable groups.

2. The coating system according to claim 1 wherein the conjugated cyclic diketone is a quinone.

3. The coating system according to claim 2 wherein the quinone is selected from substituted and unsubstituted benzoquinone, camphorquinone, naphthoquinone, and anthraquinone.

4. The coating system according to claim 1 wherein the negatively charged groups are independently selected from salts of organic acids.

5. The coating system according to claim 4 wherein the organic acids are selected from sulfonic acid, carboxylic acid, and phosphoric acid.

6. The coating system according to claim 1 wherein the nonpolymeric core molecule comprises a cyclic group.

7. The coating system according to claim 6 wherein the cyclic group is a benzene radical.

8. The coating system according to claim 1 wherein each aryl ketone is independently selected from the group consisting of acetophenone, benzophenone, anthraquinone, anthrone, and heterocyclic analogs of anthrone, including their substituted derivatives.

9. The coating system according to claim 1 comprising the coating agent as described in (a)(ii), and further comprising one or more spacer groups attaching corresponding photoreactive species to the core molecule.

10. The coating system according to claim 9 wherein the spacer groups each independently comprise a radical of the formula:

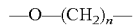
—O—(CH$_2$)$_n$— wherein n is a whole number equal to at least one.

11. The coating system according to claim 9 wherein the spacer groups each independently comprise a radical of the formula:

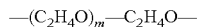
—(C$_2$H$_4$O)$_m$—C$_2$H$_4$O— wherein m is a whole number equal to at least one.

12. A coating system according to claim 1 wherein the molecules bearing polymerizable groups further comprise at least one functional group with a high affinity for water.

13. A coating system according to claim 12 wherein the functional group with a high affinity for water is selected from the group consisting of electrically neutral hydrophilic groups, negatively charged groups, and positively charged groups.

14. A coating system according to claim 1 wherein the molecules bearing polymerizable groups are selected from the group consisting of monomeric polymerizable molecules and macromeric polymerizable molecules.

15. A coating agent comprising a nonpolymeric core molecule having attached thereto, either directly or indirectly, one or more substituents comprising negatively charged groups, and two or more photoreactive species,
   wherein the photoreactive species are provided as discrete photoreactive groups, and wherein the photoreactive species include at least one first photoreactive species able when activated in the presence of a support surface, to attach the coating agent to a support surface, and at least one second photoreactive species able when activated in the presence of free radical polymerizable groups, to initiate polymerization of those groups, the second photoreactive species being able in the absence of such free radical polymerizable groups, to revert to a latent reactive state; and wherein the photoreactive species are independently aryl ketones and:
   a plurality of molecules bearing free radical polymerizable groups.

16. The coating agent according to claim 15 wherein the negatively charged groups are independently selected from salts of organic acids.

17. The coating agent according to claim 16 wherein the organic acids are selected from sulfonic acid, carboxylic acid, and phosphoric acid.

18. The coating agent according to claim 15 wherein the nonpolymeric core molecule comprises a cyclic group.

19. The coating agent according to claim 18 wherein the cyclic group is a benzene radical.

20. The coating agent according to claim 15 wherein each aryl ketone is independently selected from the group consisting of acetophenone, benzophenone, anthraquinone, anthrone, heterocyclic analogs of anthrone, including their substituted derivatives.

21. The coating agent according to claim 15 wherein the coating agent further comprises one or more spacer groups attaching corresponding photoreactive species to the core molecule.

22. The coating agent according to claim 21 wherein the spacer groups each independently comprise a radical of the formula:

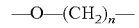
—O—(CH$_2$)$_n$— wherein n is a whole number equal to at least one.

23. The coating agent according to claim 21 wherein the spacer groups each independently comprise a radical of the formula:

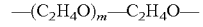
—(C$_2$H$_4$O)$_m$—C$_2$H$_4$O— wherein m is a whole number equal to at least one.

24. The coating agent of claim 15, wherein the coating agent has a solubility in water of at least about 0.1 mg/ml at room temperature.

25. The coating agent of claim 15, wherein the coating agent has a solubility in water of at least about 0.5 mg/ml at room temperature.

26. The coating agent of claim 15, wherein the coating agent has a solubility in water of at least about 1.0 mg/ml at room temperature.

27. A method of coating a support surface with a coating agent in order to provide latent reactive groups, the method comprising:
a) providing a support surface;
b) applying to the support surface a coating agent comprising two or more photoreactive species and one or more negatively charged groups, the coating agent selected from:
   i) a conjugated cyclic diketone having attached thereto, either directly or indirectly, one or more substituents comprising negatively charged groups, and wherein each ketone group of the diketone is able to serve as a photoreactive moiety capable of being activated in order to provide a free radical; and
   ii) a nonpolymeric core molecule having attached thereto, either directly or indirectly, one or more substituents comprising negatively charged groups, and two or more photoreactive species, wherein the photoreactive species are provided as discrete photoreactive groups;
wherein the photoreactive species include at least one first photoreactive species able, when activated in the presence of the support surface, to attach the coating agent to the surface, and at least one second photoreactive species able when activated in the presence of free radical polymerizable groups, to initiate polymerization of those groups, the second photoreactive species being able in the absence of such free radical polymerizable groups, to revert to a latent reactive state, and wherein the photoreactive species are independently aryl ketones;
c) illuminating the agent upon the support surface under conditions suitable to photochemically attach the coating agent to the surface by means of the first photoreactive species, and to allow the second photoreactive species to remain unbound to the support surface and to revert to their latent reactive state; and
d) providing a plurality of molecules bearing free radical polymerizable groups.

28. The method according to claim 27 wherein the coating agent provided on the support surface provides the surface with antithrombogenic properties.

29. The method according to claim 27 wherein the conjugated cyclic diketone is a quinone.

30. The method according to claim 29 wherein the quinone is selected from substituted and unsubstituted benzoquinone, camphorquinone, naphthoquinone, and anthraquinone.

31. The method according to claim 27 wherein the negatively charged groups are independently selected from salts of organic acids.

32. The method according to claim 27 wherein the organic acids are selected from sulfonic acid, carboxylic acid, and phosphoric acid.

33. The method according to claim 27 wherein the nonpolymeric core molecule comprises a cyclic group.

34. The method according to claim 33 wherein the cyclic group is a benzene radical.

35. The method according to claim 27 wherein each aryl ketone is independently selected from the group consisting of acetophenone, benzophenone, anthraquinone, anthrone, heterocyclic analogs of anthrone, including their substituted derivatives.

36. The method according to claim 27 comprising the coating agent as described in (b)(ii), and further comprising one or more spacer groups attaching corresponding photoreactive species to the core molecule.

37. The method according to claim 36 wherein the spacer groups each independently comprise a radical of the formula:

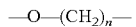
—O—(CH$_2$)$_n$— wherein n is a whole number equal to at least one.

38. The method according to claim 36 wherein the spacer groups each independently comprise a radical of the formula:

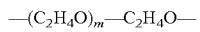
—(C$_2$H$_4$O)$_m$—C$_2$H$_4$O— wherein m is a whole number equal to at least one.

39. The method according to claim 27 wherein the coating agent is selected from the group 4,5-bis(4-benzoylphenylmethyleneoxy)benzene-1,3-disulfonic acid salt, 2,5-bis(4-benzoylphenylmethyleneoxy)benzene-1,4-disulfonic acid salt, and 2,5-bis(4-benzoylphenylmethyleneoxy)benzene-1-sulfonic acid salt.

40. A support surface bearing a coating comprising a polymer layer attached to the surface by a coating agent, the coating agent comprising the residues of two or more photoreactive species and one or more negatively charged groups, the coating agent elected from:
   i) a conjugated cyclic diketone having attached thereto, either directly or indirectly, one or more substituents comprising negatively charged groups, and wherein each ketone group of the diketone was able to serve as a photoreactive moiety capable of being activated in order to provide a free radical; and
   ii) a nonpolymeric core molecule having attached thereto, either directly or indirectly, one or more substituents comprising negatively charged groups, and the residues of two or more photoreactives species, wherein the photoreactive species were provided as discrete photoreactive groups;
wherein the photoreactive species included at least one first photoreactive species able when activated in the presence of the support surface, to attach the coating agent to the surface, and a least one second photoreactive species able when activated in the presence of free radical polymerizable groups, to initiate polymerization of those groups, the second photoreactive species being able in the absence of such free radical polymerizable groups, to revert to a latent reactive state, and wherein the photoreactive species are independently aryl ketones; and
a plurality of molecules bearing free radical polymerizable groups.

41. The support surface bearing a coating according to claim 40 wherein the conjugated cyclic diketone is a quinone.

42. The support surface bearing a coating according to claim 41 wherein the quinone is selected from substituted and unsubstituted benzoquinone, camphorquinone, naphthoquinone, and anthraquinone.

43. The support surface bearing a coating according to claim 40 wherein the negatively charged groups are independently selected from salts of organic acids.

44. The support surface bearing a coating according to claim 43 wherein the organic acids are selected from sulfonic acid, carboxylic acid, and phosphoric acid.

45. The support surface bearing a coating according to claim 40 wherein the nonpolymeric core molecule comprises a cyclic group.

46. The support surface bearing a coating according to claim 45 wherein the cyclic group is a benzene radical.

47. The support surface bearing a coating according to claim 40 wherein each aryl ketone is independently selected from the group consisting of acetophenone, benzophenone, anthraquinone, anthrone, heterocyclic analogs of anthrone, including their substituted derivatives.

48. The support surface bearing a coating according to claim 40 comprising the coating agent as described in (b)(ii), and further comprising one or more spacer groups attaching corresponding photoreactive species to the core molecule.

49. The support surface bearing a coating according to claim 48 wherein the spacer groups each independently comprise a radical of the formula:

—O—(CH$_2$)$_n$— wherein n is a whole number equal to at least one.

50. The support surface bearing a coating according to claim 48 wherein the spacer groups each independently comprise a radical of the formula:

—(C$_2$H$_4$O)$_m$—C$_2$H$_4$O— wherein m is a whole number equal to at least one.

* * * * *